United States Patent [19]

Pelosi et al.

[11] 4,059,597

[45] Nov. 22, 1977

[54] 1-[5-(2-NITROPHENYL)-2-FURANCARBOX-IMIDOYL]-1H-HEXAHYDROAZEPINE HYDROCHLORIDE

[75] Inventors: Stanford S. Pelosi; Ronald E. White; George C. Wright; Chia Nien Yu, all of Norwich, N.Y.

[73] Assignee: Morton-Norwich Products, Inc., Norwich, N.Y.

[21] Appl. No.: 763,328

[22] Filed: Jan. 28, 1977

[51] Int. Cl.$^2$ .................................... C07D 307/66
[52] U.S. Cl. .............................. 260/347.7; 424/285
[58] Field of Search ................................ 260/347.7

[56] References Cited
PUBLICATIONS

Dunlop, The Furans, ACS Monograph Series (1953), pp. 242 to 246.

*Primary Examiner*—Richard L. Raymond
*Attorney, Agent, or Firm*—Anthony J. Franze

[57] ABSTRACT

1-[5-(2-Nitrophenyl)-2-furancarboximidoyl]-1H-hexahydroazepine hydrochloride is an effective antifungal agent.

1 Claim, No Drawings

1-[5-(2-NITROPHENYL)-2-FURANCARBOX-IMIDOYL]-1H-HEXAHYDROAZEPINE HYDROCHLORIDE

This invention relates to the compound 1-[5-(2-nitrophenyl)-2-furancarboximidoyl]-1H-hexahydroazepine hydrochloride.

This compound possesses antifungal activity and is useful in the prevention of fungal growth. It is particularly inimical to Candida albicans in the commonly employed in vitro technique for determining antifungal activity at 80 mcg of compound per milliter of test media. This compound can be combined in known fashion with various compatible excipients and adjuvants to provide antifungal compositions.

The compound of this invention is readily prepared. Currently, it is preferred to react methyl 5-(2-nitrophenyl)-2-furancarboximidamide with hexamethyleneimine.

In order that this invention may be fully available to and understood by those skilled in the art, the method now preferred for making it is described:

A mixture of 5-(2-nitrophenyl)-2-furonitrile (92 g, 0.43 mole) and anhydrous methanol (1000 ml) was heated to 55° and sodium methoxide (1.5 g) was added. The steam bath was removed, the solution was stirred for 2 hours and stored overnight at room temperature. The solution was poured into ice water (1000 ml) and stirred for 1 hour. The product was collected by filtration and air dried to yield 91 g (86%) of methyl 5-(2-nitrophenyl)-2-furancarboximidate. A sample was recrystallized from isopropanol, m.p. 107°–108°.

Anal. Calcd. for $C_{12}H_{10}N_2O_4$: C, 58.54; H, 4.09; N, 11.38.

Found: C, 58.56; H, 3.87; N, 11.26.

A mixture of the above compound (33 g, 0.14 mole), ethanol (250 ml), and hexamethyleneimine (14 g, 0.14 mole) was refluxed for 8 hours and stored overnight at room temperature. The reaction mixture was filtered, the filtrate was stripped of solvent under reduced pressure, xylene was added and again stripped of solvent. The residue was dissolved in isopropanol (400 ml), the solution was adjusted to pH 2 with isopropanol/HCl, and cooled. The product was collected by filtration to yield 27 g (55%) of 1-[5-2-nitrophenyl)-2-furancarboximidoyl]-1H-hexahydroazepine hydrochloride, recrystallized from acetonitrile, m.p. 201°–203°.

What is claimed is:

1. The compound 1-[5-(2-nitrophenyl)-2-furancarboximidoyl]-1H-hexahydroazepine hydrochloride.

* * * * *